United States Patent
Thompson et al.

(10) Patent No.: US 11,183,273 B2
(45) Date of Patent: Nov. 23, 2021

(54) HETEROGENEOUS METHOD FOR MODELLING A BIOCHEMICAL ENVIRONMENT

(71) Applicant: X Development LLC, Mountain View, CA (US)

(72) Inventors: Jason Thompson, Redwood City, CA (US); Frank Russo, Sunnyvale, CA (US)

(73) Assignee: X Development LLC, Mountain View, CA (US)

( * ) Notice: Subject to any disclaimer, the term of this patent is extended or adjusted under 35 U.S.C. 154(b) by 970 days.

(21) Appl. No.: 15/694,500

(22) Filed: Sep. 1, 2017

(65) Prior Publication Data

US 2019/0073450 A1 Mar. 7, 2019

(51) Int. Cl.
*G16C 10/00* (2019.01)
*G16C 20/10* (2019.01)
*G16B 5/00* (2019.01)
*G16B 50/00* (2019.01)
*G06F 17/13* (2006.01)
*G06F 17/18* (2006.01)

(52) U.S. Cl.
CPC ............. *G16C 10/00* (2019.02); *G06F 17/13* (2013.01); *G06F 17/18* (2013.01); *G16B 5/00* (2019.02); *G16B 50/00* (2019.02); *G16C 20/10* (2019.02)

(58) Field of Classification Search
None
See application file for complete search history.

(56) References Cited

U.S. PATENT DOCUMENTS

| | | | |
|---|---|---|---|
| 2005/0042663 A1* | 2/2005 | Blinov | G16B 5/30 435/6.18 |
| 2007/0212719 A1* | 9/2007 | Hlavacek | G16B 5/00 435/6.14 |

FOREIGN PATENT DOCUMENTS

WO WO 2014/015196 A2 1/2014

OTHER PUBLICATIONS

Schulz et al. (Eurographics Workshop on Visual Computing for Biomedicine (2008); Eds. Botha, Kindlmann, Niessen and Preim; Rostock, Germany; 9 pages).*
He et al. (2010 International Conference on Computerand Communication Technologies in Agriculture Engineering—CCTAE (2010) :pp. 330-332).*
Heino, J. et al., "Bayesian flux balance analysis applied to a skeletal muscle metabolic model," Journal of Theoretical Biology, 2007, vol. 248, pp. 91-110.
PCT International Search Report and Written Opinion, PCT Application No. PCT/US2018/039127, dated Oct. 11, 2018, 16 pages.
Sharan, R. "Analysis of Biological Networks: Constraint-Based Modeling of Metabolic Networks," Lecture 10, Jan. 5, 2006, pp. 1-22.

* cited by examiner

*Primary Examiner* — Lori A. Clow
(74) *Attorney, Agent, or Firm* — Kilpatrick Townsend & Stockton LLP

(57) ABSTRACT

A method for simulating a biochemical environment utilizes a heterogeneous process model, which evaluates both a flux balance analysis and one or more detailed models each on a different but overlapping sets of molecules in the biochemical environment. The heterogeneous process model evaluates the flux balance analysis based on a stoichiometric matrix, a flux vector including initial internal exchange flux values, and an objective function. The heterogeneous process model evaluates the one or more detailed models based on an initial set of molecule concentrations and a plurality of detailed model parameters. The results are then used to update the exchange fluxes and molecules concentrations. The process is repeated thereby integrating the results of the flux balance analysis with the one or more detailed models.

33 Claims, 7 Drawing Sheets

HETEROGENEOUS METHOD FOR MODELLING A BIOCHEMICAL ENVIRONMENT

TECHNICAL FIELD

This application relates generally to the simulation of biochemical environments and the field of bioprocess engineering.

BACKGROUND

Flux balance analysis (FBA) has been a staple in the field of bioprocess engineering due to its low input data requirements and its computational efficiency. However, the number of applications for which FBA is useful remains small, due to the limitations imposed by the steady state and optimality assumptions of the model. Thus, the use of FBA alone is not satisfactory for a large number of bioprocess engineering applications that would benefit from an accurate simulation of a biochemical environment or process.

SUMMARY

A method for heterogeneously modelling processes and reactions in a biochemical environment integrates a flux balance analysis (FBA) of a set of biochemical processes with one or more detailed mathematical models of a subset of those processes. This multiple-model structure is herein referred to as a heterogeneous process model. Depending on the embodiment, the detailed time-dependent models may include ordinary differential equation (ODE) models, Monte Carlo simulations, and stochastic differential equation (SDE) models, or any other model or simulation that can predict the behavior of a biochemical environment. The heterogeneous model utilizes internal exchange fluxes in the FBA that provide an interface between the larger FBA and the more detailed time based models. The heterogeneous model is evaluated once per time step based on a state vector of fluxes and concentrations that describe the biochemical environment. In one particular implementation, the FBA and the detailed models are evaluated in parallel based on the results of the previous time step to better model dynamic behavior in the biochemical environment.

The heterogeneous process model utilizes a biochemical database storing a set of molecules and processes involved in a biochemical environment. In some embodiments, the biochemical database is organized as bipartite graph that includes molecule nodes and process nodes connected by edges indicating the role of each associated molecule node in the associated process node.

The heterogeneous process model may also utilize a configuration file as input indicating the scope and parameters for the model. In some embodiments, the configuration file designates the molecules and/or processes from the biochemical database that will be included in the model. The configuration file also contains a model designation file that designates the scope of the FBA by indicating the processes that will be included in the FBA flux vector and molecules that will be included in the stoichiometric matrix of the FBA. The model designation file also defines input and output exchange fluxes to the FBA as well as initial values for the internal exchange fluxes of the heterogeneous model. The configuration file may also include a set of initial conditions for the biochemical environment being simulated by the model, these initial conditions may include the temperature and/or pressure of the environment as well as an initial state vector indicating the concentration of each molecule being simulated by the model. Additionally the configuration file may include initial values for exchange fluxes to allow the heterogeneous model to evaluate at a first time step. The objective function of the FBA may also be determined by the configuration file.

The heterogeneous process model is compiled using the configuration file and generates a stoichiometric matrix, a state vector (including a flux vector and mass vector), and sets the initial conditions for the detailed models. The model then proceeds by evaluating the detailed models and FBA in parallel. After the first time step evaluation is complete, the results of the detailed models are used to set the internal exchange fluxes back into the FBA, while the results of the FBA are used to set the internal exchange fluxes into the detailed models. Both types of models are evaluated in parallel for a second time and the process continues until the model satisfies some set of completion criteria.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Heterogeneous Process Model

Figure 1:
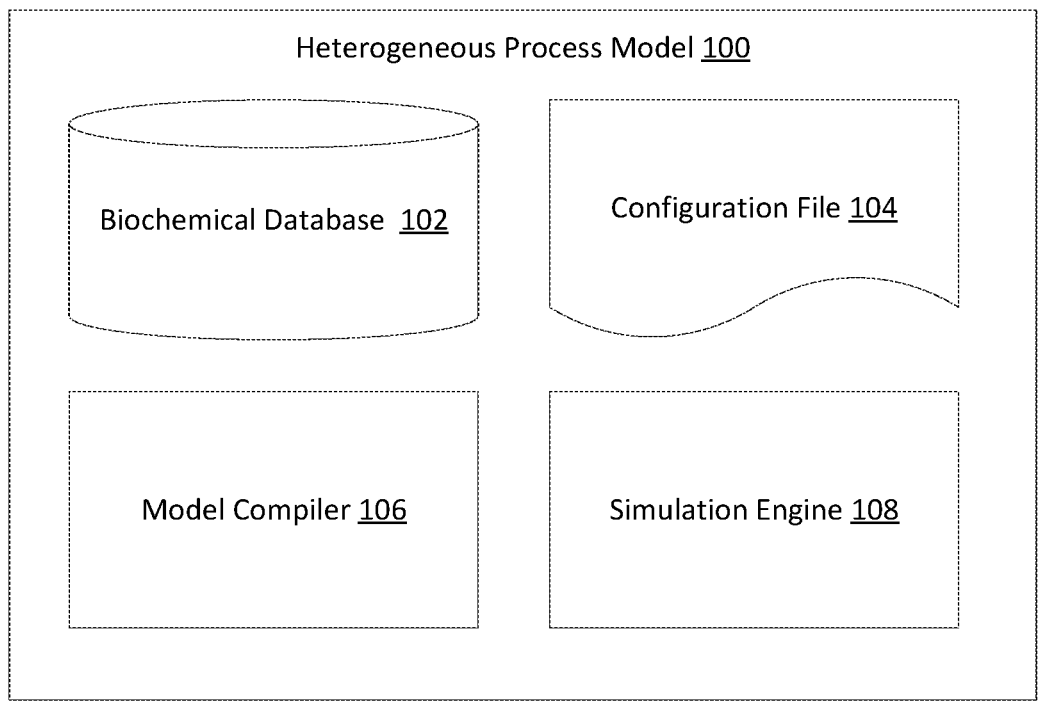
FIG. 1 is a block diagram illustrating computational components of a heterogeneous process model in accordance with one embodiment.

FIG. 1 is a block diagram illustrating computational components of a heterogeneous process model 100 in accordance with one embodiment. The heterogeneous process model 100 may be organized into four separate computational components, although other implementations may include fewer or greater numbers of computational components. Depending on the embodiment, each component of the heterogeneous process model 100 may implemented on one or more servers or other computational devices that are configured to communicate over a network (e.g. the Internet, a local area network, etc.). Alternatively, all computational components may be locally present on a single computational device. The four computational components comprising the heterogeneous process model 100 shown in FIG. 1 are a biochemical database 102, a model configuration file 104, a model compiler 106, and a simulation engine 108.

Figure 2:
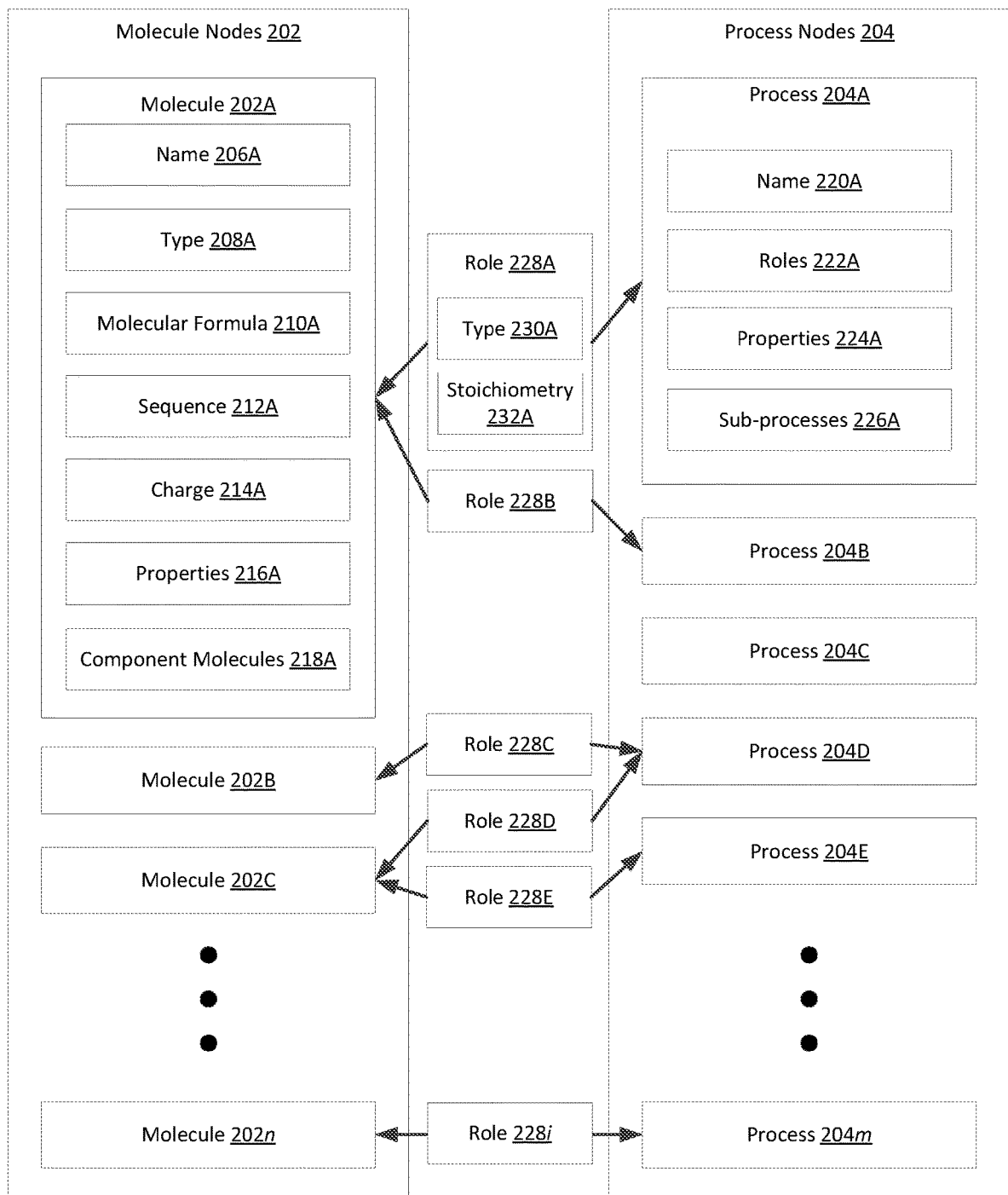
FIG. 2 is a block diagram illustrating a bipartite biochemical database in accordance with one embodiment.

In accordance with this embodiment, the biochemical database 102 is a database that stores data on molecules and processes that may be present or may occur in a biochemical environment simulated using the heterogeneous process model 100. The biochemical database 102 stores compositional data for each molecule that may be of use in the simulation, as well as data specifying how each molecule may be involved in one or more processes simulated by the heterogeneous process model 100. Although any database structure may be used to implement the biochemical database 102, FIG. 2 illustrates an exemplary bipartite biochemical database 200 that may be used in the heterogeneous process model 100 as the biochemical database 102. Those of skill in the art will recognize that the same biochemical information stored in the specified bipartite biochemical database 200 could be stored in a more generic biochemical database 102. The bipartite biochemical database 200 is described in additional detail with reference to FIG. 2.

The configuration file 104 is a set of instructions for configuring the heterogeneous process model 100. In some embodiments, the heterogeneous process model 100 may be configured to simulate a single set of processes and, therefore, is not configured separately for each use of heterogeneous process model 100. In other embodiments, the configuration file 104 is used to select the molecules and processes to be simulated in the heterogeneous process model 100. Additionally, the configuration file 104 may designate the processes to be included in the FBA component of the model and the processes to be modelled in the one or more detailed models included in the heterogeneous process model 100. Furthermore, the configuration file 104 may include parameters for the FBA and the detailed models included in the heterogeneous process model 100, as well as a set of initial conditions for each of those models. The configuration file 104 is further described with respect to FIG. 4.

The model compiler 106 may use configuration file 104 to compile the heterogeneous process model 100 so that a simulation can be completed. The model compiler 106 may interface with the biochemical database 102 to retrieve the necessary data for the FBA and detailed models included in the heterogeneous process model 100. The model compiler 106 uses the data retrieved from the biochemical database 102 and the configuration file 106 to generate the stoichiometric matrix, flux vector, objective function, and constraints for the FBA model. In some embodiments, the model compiler 106 also provides the necessary data to the detailed models included in the heterogeneous process model 100. A method for compiling the heterogeneous process model 100 is further described with respect to FIG. 5.

The simulation engine 108 performs the calculations required to simulate a biochemical process using the heterogeneous process model 100, optionally configured by the model compiler 106. The simulation engine 108 may initialize the heterogeneous process model 100 using the initial conditions supplied in the configuration file 104. Alternatively, if the simulation engine 108 is configured to simulate a specific biochemical environment, the simulation engine 108 may initialize the heterogeneous process model 100 without a configuration file 104. The simulation engine 108 creates an initial state vector, which includes the concentration of each molecule included in the heterogeneous process model 100 and, optionally, any initial internal exchange flux values for the initial evaluation of the FBA. The simulation engine 108 may then evaluate the detailed models and perform the FBA in parallel. In embodiments where the detailed models do not have steady state solutions, the simulation engine 108 may find the solution of the detailed model for a first time step after the initial state, where the time step is of a predetermined length. After determining the solution for each detailed model, including the concentrations of the molecules being simulated in each detailed model, the flux of the processes being simulated by each detailed model, and any changes to the overall biochemical environment (e.g. temperature changes, pH changes, etc.) caused by the processes being simulated by each detailed model, the simulation engine 108 updates the initial state vector with the solution data. The simulation engine 108 also may use the fluxes determined during the evaluation of the FBA multiplied by the length of the predetermined time step to determine the new concentrations of the molecules included in the FBA. Thus, the simulation calculates a state vector for the first time step using the results of both the FBA and the detailed models.

The simulation engine 108 also calculates the exchange fluxes that connect the detailed models with the overall FBA and allows for integration between the FBA and the one or more detailed models included in the heterogeneous process model 100. The internal exchange fluxes calculated in the first time step are then used by the simulation engine 108 in the evaluation of the FBA for the second time step. The simulation engine 108 continues this process for a user determined number of time steps or until a user provided termination state is reached. The functions of the simulation engine 108 are further described with respect to FIG. 6.

II. Bipartite Biochemical Database

FIG. 2 is a block diagram illustrating a bipartite biochemical database in accordance with one embodiment. The bipartite biochemical database 200 is one example of a biochemical database 102 for use by the heterogeneous process model 100. The bipartite biochemical database 200 contains data representing the composition and behavior of one or more biochemical environments that may be simulated using the heterogeneous process model 100. Examples of biochemical environments may include, an intracellular environment, the environment in a particular organelle of a cell, an entire cell, intercellular environments or any similar environment found in biology or that might be imagined in a biological simulation. The bipartite nature of the database refers to the two types of database objects or nodes that comprise the database, which may be categorized as "molecule nodes" 202 and "process nodes" 204. Molecule nodes 202 may represent any molecule or other physical particle present in a biochemical environment including atomic elements, ions, compounds, nucleic acids, proteins, and other macromolecules. Process nodes 204 may represent chemical reactions, protein folding, transport, regulatory interactions, active site binding, or any other physical or chemical process that may occur in a biochemical environment. The bipartite biochemical database 200 is organized in a graph structure where the abovementioned two categories of nodes are connected by edges. Each edge is referred to herein as a "role" 228 and associates a single molecule node 202 with a process node 204, thereby creating a bipartite graph of molecule 202 and process 204 nodes.

A bipartite biochemical database 200 may be implemented using a variety of non-relational database software options. Embodiments utilizing non-relational databases provide advantages in allowing for increased flexibility in the creation of nodes representing biochemical molecules and processes. Biochemical environments typically include molecules of several different types, for example, macromolecules such as nucleic acid chains and proteins in addition to simple compounds such as water and glucose. Due to the diversity in the types of molecules, a non-relational database may be used to allow for documents (e.g., JSON, XML, or other formats) to represent the nodes and edges of the bipartite biochemical database 200. Alternatively, a graph specific database technology or any other suitable database framework may be used to implement the bipartite biochemical database 200. Those of skill in the art will appreciate the database structure described herein may be implemented using a variety of available database software options. Additional benefits of the graph structure of the bipartite biochemical database 200 are further described below.

Each molecule node 202 contains metadata fields that provide information about the molecule represented by the node that is pertinent to the behavior of the represented molecule in biochemical environments. These metadata fields may include a molecule name 206, molecule type 208, a molecular formula 210, a molecular sequence 212, a molecular charge 214, molecular properties 216, and component molecules 218. FIG. 2 illustrates molecule nodes 202A, 202B, 202C, through 202n and illustrates the metadata fields 206A, 208A, 210A, 212A, 214A, 216A, and 218A corresponding to molecule node 202A. However, each of the other illustrated molecule nodes 202 may also contain the same or similar metadata fields.

A molecule node 202 need not contain data for each of the above metadata fields and, depending on the embodiment, fewer or additional fields may be included in a molecule node 202 as needed for the particular detailed models included in the heterogeneous process model 100. In some embodiments, a unique ID may be assigned to each molecule node 202 for easier querying and referencing in the database. Because the various types of molecules found in a biochemical environment vary in their complexity and regimes of interaction with other molecules, different fields may be applicable to each type of molecule. As such, some of the abovementioned fields may be left empty for molecule nodes 202 of a certain type despite being present in the data structure of the molecule node 202.

In some examples, the molecule name field 206 of the molecule node 202 contains a human identifiable string indicating the molecule represented by the molecule node 202. The name 206 chosen for a molecule node 202 may be determined by a user entering data into the bipartite biochemical database 200 or it may be automatically generated based on other metadata provided for the molecule. Various naming schemes for biochemical molecules, known to those skilled in the art, may be used to ensure consistency for the name 206 of each molecule node 202.

In some examples, the molecule type field 208 indicates the category of molecule to which the represented molecule belongs. The categories are typically set based on the application of the bipartite biochemical database 200 and each molecule may be assigned a type upon entry into the bipartite biochemical database 200. The type field 208 itself may contain a string or type ID number indicating the category to which the molecule represented by the molecule node 202 belongs. Examples of potential categories for a molecule may include, ion, atomic element, compound, organic compound, nucleic acid (DNA, RNA, etc.), amino acid chain, protein, etc. In some embodiments, an application utilizing the bipartite biochemical database 200 may reference the type 208 of a molecule node 202 to determine which properties 216 or other metadata that may be retrieved from the molecule node 202. For example, if the molecule represented by the molecule node 202 has a type 208 indicating that it is a "protein" any application accessing the molecule node 208 may be configured to retrieve protein structure, binding site information, and an amino acid sequence from the properties field 216 of the molecule node 202. In an alternative example, if a molecule node 202 has a type 208 indicating that it is a compound, an application accessing the molecule node may be configured to retrieve a molecular formula, molecular weight, solubility, and/or other information from the molecule node 202.

In some examples, the type 208 of a molecule node 202 may indicate the structure of the node itself. For example, the metadata fields present in the molecule node 202 may correspond to the assigned type 208 of the molecule node. For example, the metadata field indicating the sequence of a molecule may only be present in the structure of the node if it has been categorized with the type 208 corresponding to a nucleic acid, amino acid chain, or protein. This could be achieved by requiring an input to the type field 208 when adding a molecule node 202 to the bipartite biochemical database 200 and, when initializing a molecule node 202 in the bipartite biochemical database 200, structure the molecule node 202 based on the received type 208.

In some examples, the molecular formula field 210 indicates the molecular or chemical formula of a molecule represented by a molecule node 202. The molecular formula 210 may be a string indicating the atomic elements comprising the represented molecule or, in the case of some types of molecules, may be a string that indicates that the molecular formula is variable or not applicable to the behavior of the molecule in a biochemical environment of interest. In some embodiments, the molecular formula 210 is represented in a standardized format that conforms to specific molecular formula conventions known in the art. In some embodiments, the molecular formula may also indicate the charge of the molecule or have modifiers associated with the string indicating additional details about the molecular structure of the represented molecule. For example, an additional string may be provided indicating the particular isomer of a compound with multiple isomers (in other embodiments, this information is provided in the properties filed 216).

In some examples, the sequence field 212 indicates the sequence of a molecule represented by a molecule node 202. Not all types of molecules contain sequence information but the nucleotide sequence of nucleic acid or the amino acid sequence of a protein may be the most biochemically relevant way to describe the molecule. Therefore, sequence information may only be present in the sequence field 212 if the molecule represented by the molecule node is a biopolymer of some kind. The sequence information 212 is typically a string indicating the order of the monomers comprising the represented molecule. The sequence information may use a standard notation corresponding to the type 208 of molecule represented by the molecule node 202. For example, if the molecule node 202 represents a strand of DNA and is labeled as having a type 208 of "DNA" the sequence information 212 would be a string including a sequence of A's, T's, C's, and G's representing adenine, thymine, cytosine, and guanine respectively. In an alternative example, a molecule node 102 representing a protein may include sequence information 212 indicating the amino acid sequence for the protein.

In some examples, the charge field 214 indicates the electrical charge of the molecule represented by the molecule node 202. The charge field 214 may be comprised of an integer value of indicating the electrical charge of the molecule. For example, if the molecule node represents a hydrogen ion the charge field 214 would indicate a "1" indicating a positive charge. In some cases, the charge of a molecule may be variable especially if the molecule is a macro molecule and may occur in a number of different states, in which case the charge field 214 would have a value indicating that the charge was variable. In some cases, the charge of a molecule represented by a molecule node 202 may not be applicable to its behavior in a biochemical environment, therefore, in some embodiments, the charge field 214 may contain a string indicating as such.

In some examples, the properties field 216 provides information regarding the relevant chemical and physical properties of a molecule represented by a molecule node 202. In some embodiments, the contents of the properties field 216 may be a key-value pair array indicating the relevant property and its corresponding value. The properties listed in the properties field 216 may vary depending on the type of the molecule indicated by the type field 208. Small molecules and compounds, for example, may have properties 216 indicating standard physical properties associated with the represented molecule including, for example, a melting point, molar mass, density, solubility, acidity, enthalpy of formation, or any other relevant chemical and physical property. In some embodiments, the properties field 216 may contain null values for each property that is not known or not relevant to a particular molecule. In larger macromolecules, other properties such as the binding state of a protein, the folding state of the protein, the methylation state of a DNA strand, and other relevant macro molecular properties may be indicated in the properties field 216. Additionally, some properties may be devoted to describing interactions between the represented molecule and other molecules. For example, the active site of a protein or the binding domain of a DNA strand may be described within the properties field 216. In other embodiments, these properties may be represented in additional metadata fields in a molecule node 202.

In some examples, the component molecule field 218 indicates molecules that comprise the molecule represented by a molecule node 202. Component molecules may be any molecule that might contribute to the formation of the represented molecule and they may be represented by a string indicate the names 206 of each component molecule. Some examples include molecules that may occupy a binding site of a protein, nucleotides that comprise a nucleic acid, components of a molecular compound, conjugate bases of a particular acid, etc. The component molecule field 218 may include a list of strings indicating the component molecules or, in some embodiments a list of unique ID numbers indicating the component molecules.

FIG. 2 illustrates a number of molecule nodes 202A, 202B, 202C, through 202n and depending on the database technology used can be extended to include any number of molecule nodes 202, as needed for the application of the bipartite biochemical database 200.

In addition the molecule nodes 202, the bipartite biochemical database 200 also includes process nodes 204. As previously described, process nodes 204 may describe any type of physical or chemical process that may occur in a biochemical environment. Each process node 204 contains metadata fields describing the process represented by the process node 204, including but not limited to a process name 220, roles in the process 222, properties of the process 224, and sub-processes of the process 226. Like the molecule nodes 202 in the bipartite biochemical database 200, depending on the particular process being represented the metadata fields of the process node 204 may be empty where the metadata of the field would not be applicable.

In some examples, the name data field 220 contains a human recognizable string identifying the process represented by the process node. Like the name field 206 of the molecule node 202, in some embodiments, an ID number for the process may be included in addition to the name 220 of the process node 220. In some embodiments, the name 220 or corresponding unique ID may be used as a reference to the associated process node 220 in the bipartite biochemical database 200.

In some examples, process nodes 204 include a role metadata field 222, which lists the roles of molecules in the process represented by the process node 204. Processes that occur in biochemical environments operate on at least one molecule or other element in that environment. However, not all molecules involved in a process necessarily have the same "role" in that process. For example, most chemical reactions have a set of substrate molecules needed to initiate the reaction and a set of products that are generated as a result of the reaction. Thus, molecules that are associated with a process are characterized based on the role of the associated molecule in the process. In some embodiments, the following classifications of roles may be included in the bipartite biochemical database: substrate/reactant, catalyst, product, or cofactor. In embodiments that include process nodes 204 that represent physical processes, the same molecule may be included in multiple roles. For example, if a process node 204 represents the transportation of a protein from the endoplasmic reticulum of a cell to the Golgi apparatus the role field 222 might have two roles including a "departing molecule" and a "destination molecule." Each of these two roles would be satisfied by the same molecule, though the molecule might be represented by two separate molecule nodes 202 each representing the molecule in a different location in the cell. Embodiments that include physical processes represented as process nodes 204 may enable applications utilizing the bipartite biochemical database 200 to create more detailed simulations of a biochemical environment, which account for both chemical and physical transitions of the molecules found in the biochemical environment.

The structure of the data in the role field 222 may be an array including pairs of strings identifying the type of role and the molecule that satisfies that role in the represented process. In other embodiments, other data structures known in the art may be used to store the same information. The role metadata field may reference a molecule node 202 representing the molecule listed in the role field 204. Alternatively, the role field 222 may include references to role edges 228 that represent roles played by molecules in processes of the bipartite biochemical database 200.

In some embodiments, the process properties field 224 lists properties of the process represented by the process node 204. Processes that occur in a biochemical environment have a variety of properties that may be of interest for the purpose of simulation or data collection. Thus, the bipartite biochemical database 200 may store properties in an array or other data structure in the properties field 224 of a process node 204. In the case of chemical reactions, activation energy, Gibbs free energy change, kinematic properties and other thermodynamic properties known in the art may be included in the properties field 224. For physical processes, which may include protein folding operations and the movement of molecules in an intracellular environment in addition to any other physical process that may occur in a biochemical environment may be listed in the properties field 224.

In some embodiments, the sub-process field 226 stores sub-processes of the process represented by the process node 204. Many processes that occur in a biochemical environment may occur in multiple steps. Especially for the purpose of reaction rate determination (through identification of a rate limiting step) it is useful to maintain information of sub-process comprising a process represented by a process node 204. The sub-processes 226 may be referenced by name 220 or unique ID number and will typically have a separate node in the bipartite biochemical database.

The two types of nodes in the bipartite biochemical database 200 are associated with each other using edges, referred to herein as "roles" 228, that represent the role an associated molecule plays in an associated process. The roles 228 themselves may be structured such that they contain direct pointers to the associated molecule node 202 and the associated process node 204. In addition to containing pointers to the associated molecule node 202 and the associated process node 204, the role object 228 may also contain metadata indicating the type of role 230 that the molecule represented by the associated molecule node 202 plays in the process represented by the associated process node 204. Additionally, the role 228 contains the stoichiometry value of the represented molecule in the represented process. These edges 228 ensure that in applications involving the simulation of a biochemical environment accurate stoichiometric relationships are maintained in each reaction. In some embodiments, roles 228 may have a defined directionality in the graph. The directionality may indicate whether the molecule represented by the associated molecule node 202 is being consumed or produced in the process represented by the associated process node 204. The directionality of a role 228 in the bipartite biochemical database may be related to the role type described below. In embodiments with role directionality, mathematic techniques utilizing directed graphs can be utilized by applications utilizing the bipartite biochemical database.

As previously described with respect to the roles field 222 in the process node 204, the roles type 230 may be one of substrate/reactant, catalyst, product, or cofactor for chemical processes and may be any applicable role in a physical process that would accurately described the behavior of the associated molecule in the associated physical process. The role type 230 may be stored as a string describing the role type or by any other effective means known in the art. In embodiments utilizing a directed graph, the directionality of a role 228 may correspond to the role type 230. For example, a role type 230 of substrate/reactant would result in a directionality from the associated molecule node 202 to the associated process node 204 while a role type 230 of product would result in a directionality flowing from the associated process node 204 to the associated molecule node 202. Other role types 230 such as catalyst or cofactor may corresponding a bidirectional role edge 228 because the molecule represented by the molecule node 202 remains present before and after the associated process occurs.

In some examples, the stoichiometric coefficient metadata field 232 stores the stoichiometric coefficient of the associated molecule in the associated process. The stoichiometric coefficient indicates the ratio of each molecule having a role in a particular process and provides a framework for determining the flux of molecules in a biochemical environment. The stoichiometric coefficient 232 of a role 228 may be indicated by a positive integer equal to the value of the stoichiometric coefficient in a chemical equation representing the process associated with the role 228. For physical processes, the stoichiometric coefficient may instead be based on whatever physical interaction between molecules is being represented by the associated process.

FIG. 2 illustrates n molecule nodes 202 including molecule nodes 202A, 202B, 202C, m process nodes 204 including process nodes 204A, 204B, 204C, 204D, and 204E, and i role edges 228 including 228A, 228B, 228C, 228D, and 228E. This illustrates that there may be differing numbers of molecule nodes 202, process nodes 204, and role edges 228 and that there need not be a one to one matching of molecule nodes 202 to process nodes 204. Additionally, as demonstrated by the arrows illustrating example connections between molecule nodes 202, roles 228, and process nodes 204, molecule node 202 may be associated with multiple process nodes 204 and vice versa. For example, molecule node 202A is illustrated as being connected to both process node 204A and process node 204B through roles edges 228A and 228B respectively. Thus, based on the illustrated mapping, the molecule represented by molecule node 202A is involved in the processes represented by both process nodes 204A and 204B.

The structure of the bipartite biochemical database 200 offers many advantages with regard to the simulation and understanding of biochemical environments. The graph based structure comprised of edges using direct pointers allows for the quick transversal of the graph during the compilation process of the heterogeneous process model 100. Thus, given a chemical composition of an environment to be simulated, the model compiler 106 can use the bipartite biochemical database 200 to determine the chemical and physical processes that might occur in that environment. The model compiler 106 may accomplish this by quickly traversing the graph, starting from the molecules nodes 202 associated with the chemical composition of the environment. Alternatively, if a user has selected a set of processes are to be simulated by the heterogeneous process model 100, the set of molecules involved in those processes can be identified through a graph traversal starting at the processes nodes 204 corresponding the selected processes.

III. Flux Balance Analysis: Discussion of Prior Art

Figure 3A:
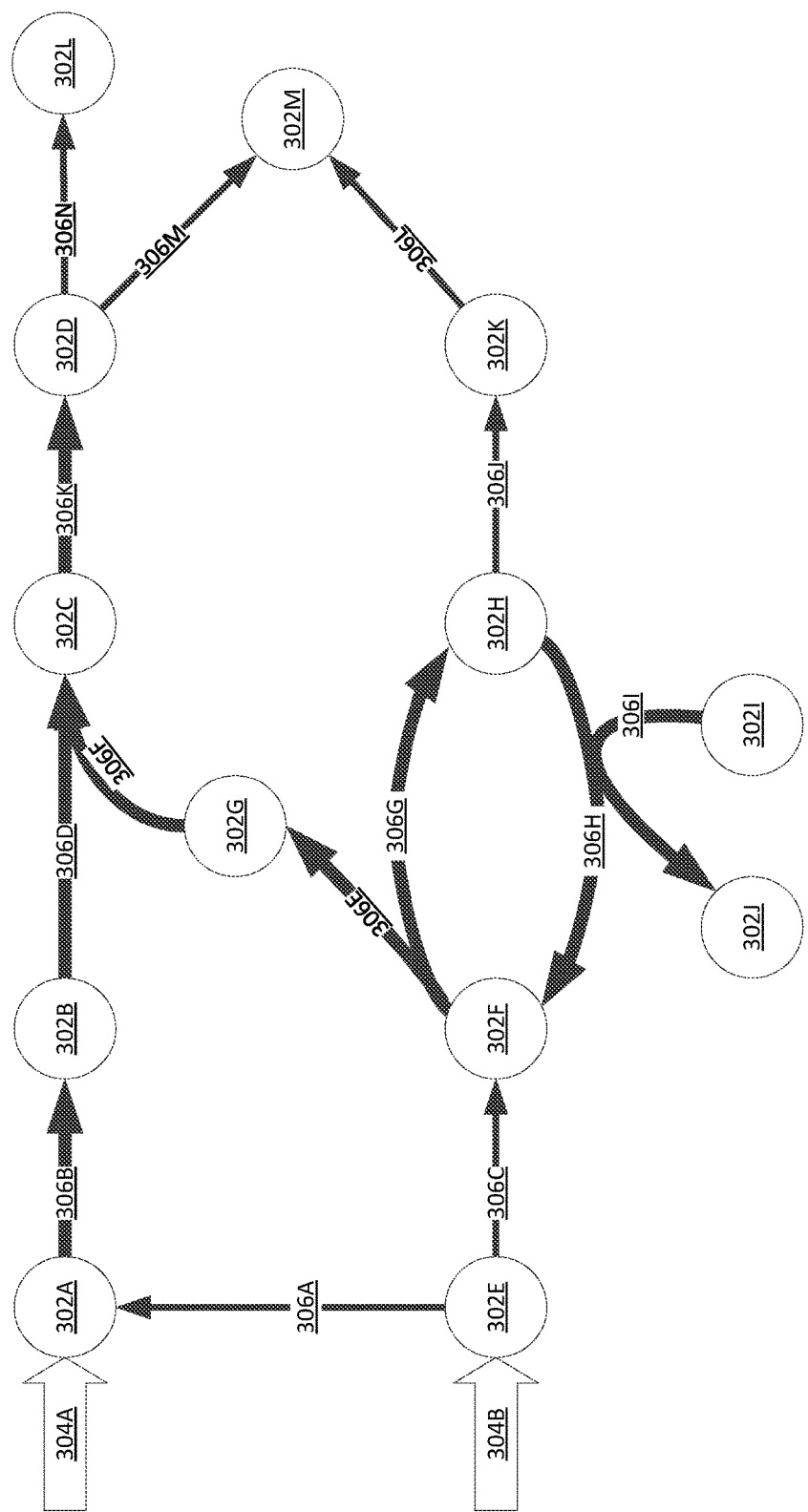
FIG. 3A is a conceptual illustration of a flux balance model for a set of processes consistent with practice known in the art.

FIG. 3A is a conceptual illustration of a flux balance model 300 for a set of processes consistent with practice known in the art. The illustration of FIG. 3A shows the solution to an FBA for a set of molecules 302A-302M (illustrated as circles) undergoing fluxes 306A-306N (illustrated as opaque arrows) and constrained by external exchange fluxes 304A and 304B (illustrated as hollow arrows). The illustrated flux balance model 300 is an example of a solution to a hypothetical FBA problem and many other possible configurations of molecules and processes can be solved using FBA. This example has been contrived in order to emphasize the improvements made by the heterogeneous process model 100 to traditional FBA.

In FIG. 3A the thickness of each arrow representing a flux 306 indicates the magnitude of the flux. Additionally, a biochemical process may involve one or more fluxes since one or more molecules are associated with the process. In this flux balance model 300 the fluxes 306 shown may not be the only fluxes between the molecules 302 and may be simplified for ease of illustration. Conventional FBA uses the stoichiometric relationships between the molecules 302 and the processes those molecules are involved in to create a linear system of equations (typically expressed as a stoichiometric matrix and a flux vector, where the stoichiometric matrix is comprised of linear coefficient for the fluxes to be solved for) along with an objective function that is used to resolve the under-defined linear system of equations created by those stoichiometric relationships. External exchange fluxes 304A and 304B define the magnitude of the flux coming into the biochemical system simulated by the FBA and serve as the input to the simulation. External exchange fluxes 304 are typically set to known biologically accurate values or reasonable estimates so that the FBA solution can be solved more accurately.

For this approach to be accurate with respect to the underlying biochemical processes FBA attempts to model, FBA makes a steady state assumption because of the analytical framework used by FBA, which provides only a single value for each flux being analyzed. As a result, the specific concentration of each of the molecules 302A-302M is not needed to perform FBA. Additionally, the objective function must be biologically significant so that the solution to the FBA is solved based on a biology-based constraint on the system as opposed to an arbitrarily-imposed one. By making these assumptions, FBA can be used to simulate a biochemical system with little computational effort. However, FBA cannot account for any dynamic, thermochemical, or kinetic effects that might be significant in a biochemical system.

For example, one typical problem encountered while using FBA is that the solution may favor fluxes that result in biologically important products but that are highly energy intensive, and therefore not biologically possible. Frequently, this tendency can result in a "futile cycle" where the FBA solution indicates a high flux through a particular cycle that would not be energy efficient in a real environment. Although constraints can be applied to limit particular fluxes, without extensive knowledge of the process involved, little can be done, using conventional methods, to create an accurate solution in these cases.

FIG. 3A illustrates one such example of a futile cycle in the process included fluxes 306G and 306H between nodes 302F and 302H. Although the stoichiometric matrix and object function are not shown in this example, it can be assumed that the objective function favors the production of one of the molecules involved in the cycle resulting in high flux through the cycle. In addition to futile cycles, many other factors may result in an inaccuracy in an FBA solution. However, because of the computational inefficiency of other more detailed models FBA remains an attractive option for large scale simulation of biochemical environments.

IV. Heterogeneous Process Model: Conceptual Description

Figure 3B:
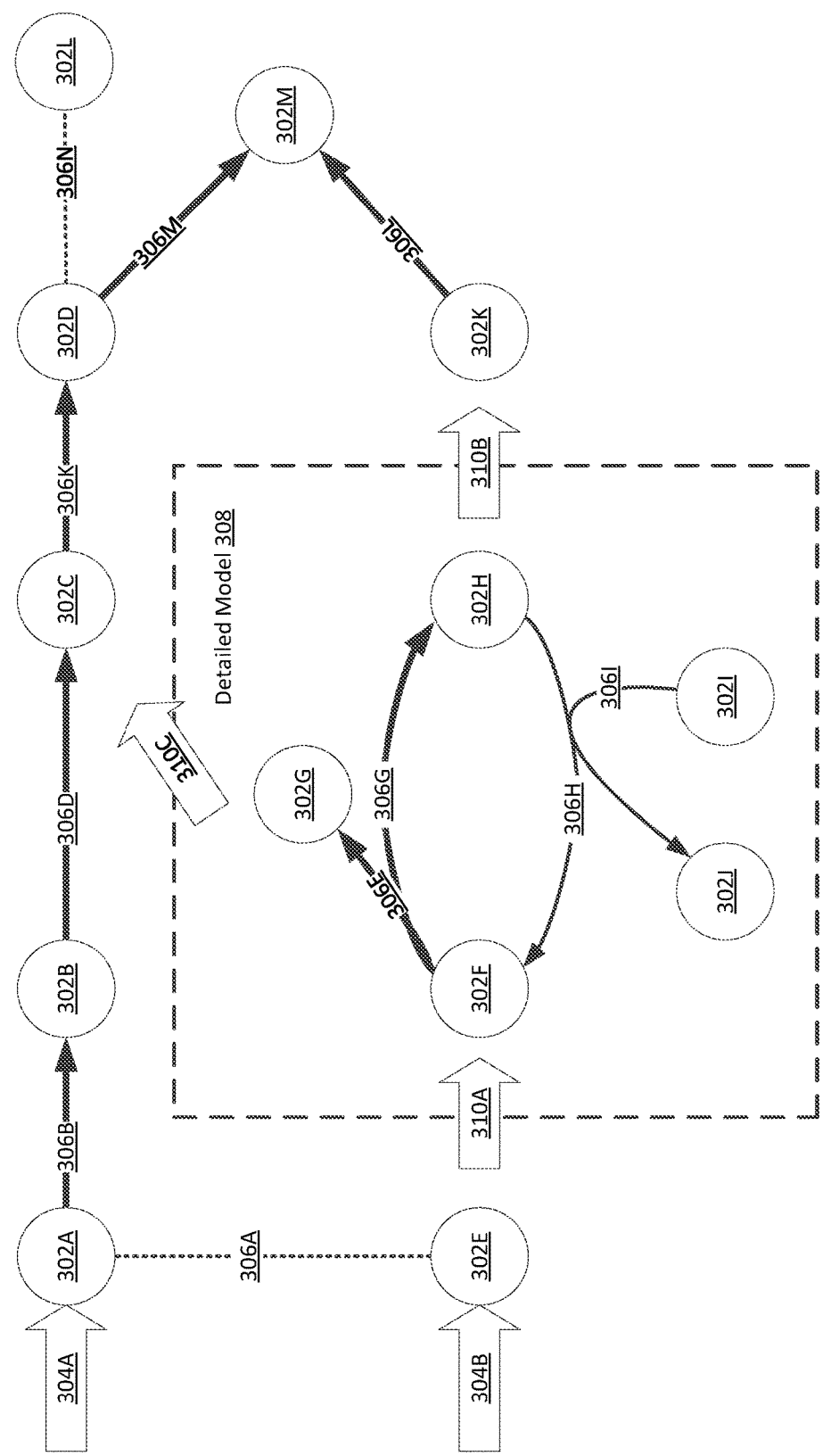
FIG. 3B is a conceptual illustration of a heterogeneous process model for the same set of processes illustrated in FIG. 3A in accordance with one embodiment.

FIG. 3B is a conceptual illustration of a heterogeneous process model 100 for the same set of processes illustrated in FIG. 3A in accordance with one embodiment. The heterogeneous process model 100 allows for the use of more detailed models in conjunction with a FBA model in order to lower the computational intensity of the simulation while increasing the accuracy of the simulation with regard to more complex processes. The heterogeneous process model 100 also lends itself to modeling more dynamic systems than can be accomplished with conventional FBA.

In the example application of the heterogeneous process model 100 illustrated in FIG. 3B, the molecules 302F-302J and the fluxes 306E and 306G-306I are simulated using a detailed model 308, while the other fluxes 306 and molecules 302 in the system are simulated using an FBA. Detailed models 308 utilized by the heterogeneous process model 100 may include ordinary differential equation (ODE) models, Monte Carlo simulations, and stochastic differential equation (SDE) models, or any other model or simulation that can predict molecular flux in a biochemical environment. In the example application of the heterogeneous process model 100 illustrated in FIG. 3B, only one detailed model 308 is being used. However, any number of detailed models 308 may be included in the heterogeneous process model 100. Detailed models 308 are typically time dependent and may utilize a larger number of variables describing the biochemical environment, including the concentration of each molecule in the biochemical environment and environmental factors like temperature. In some embodiments, detailed models 308 may result in a steady state solution for the simulated subsystem. Thus, detailed models 308 in the heterogeneous process model 100 may be used to describe both steady state and dynamic characteristics of a biochemical environment. In order to integrate a detailed model 308 with an FBA the heterogeneous process model 100 utilizes internal exchange fluxes 310 to the FBA model. The detailed models 308 determine the value of the internal exchange fluxes which are then integrated into an FBA model. This process may be completed iteratively to simulate a dynamic system or just once to determine a steady state solution, if one can be found for each of the detailed models 308 included in the heterogeneous process model 100.

In the example application of the heterogeneous process model 100 illustrated in FIG. 3B, the detailed model 308 interfaces with the larger FBA through internal exchange fluxes 310A, 310B, and 310C. The heterogeneous process model 100 evaluates each model in parallel in a process which is further described with respect to FIG. 6. FIG. 3B indicates the more realistic modelling of the system by showing the reduced flux through the cycle within the detailed model 308, which can be assumed to more realistic in this example, for example by taking into account energy requirements for particular reactions. Additionally, the detailed model 308 is used to set the internal exchange fluxes 310A-310C for the FBA. This results in a change in the FBA solution for fluxes 306A, 306B, 306D, 306K, 306L, 306M, and 306N. In this manner, detailed models 308 can be used to replace parts of an FBA model that require a more detailed analysis and the heterogeneous reaction model 100, which in turn can be used to increase the accuracy of the surrounding FBA model.

V. Compilation File

Figure 4:
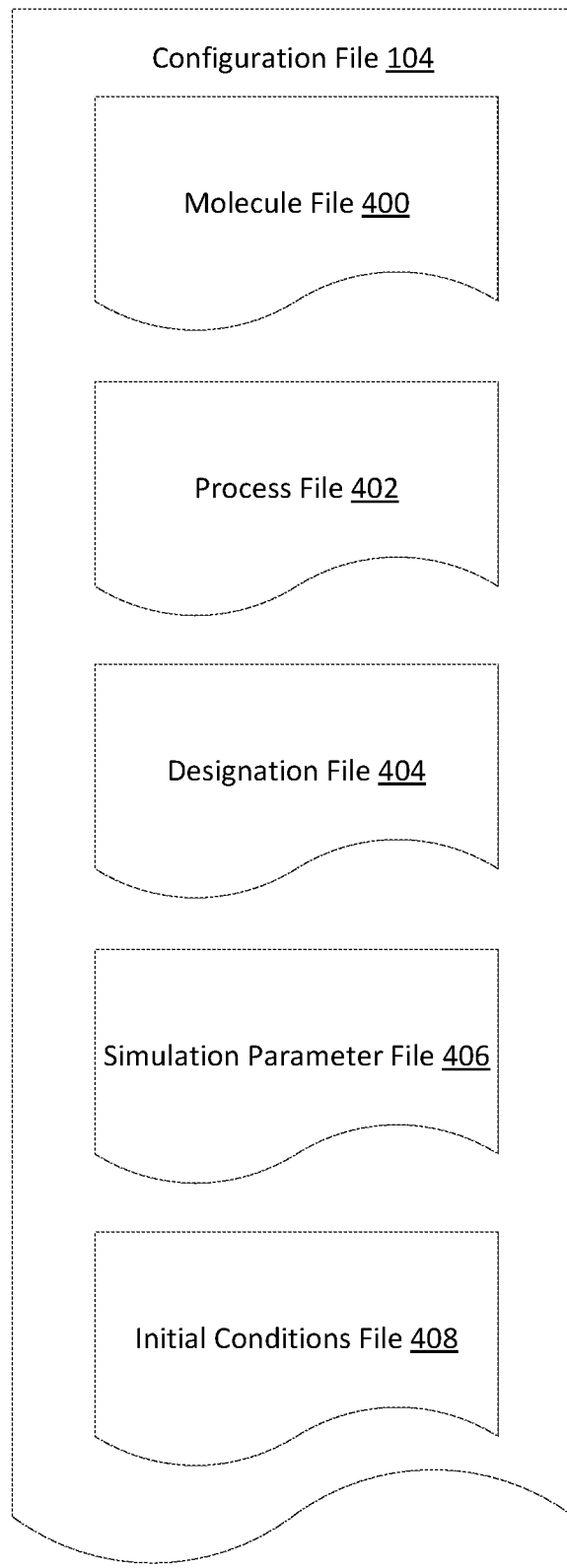
FIG. 4 is a block diagram illustrating components of a configuration file for a heterogeneous process model in accordance with one embodiment.

FIG. 4 is a block diagram illustrating components of a configuration file 104 for a heterogeneous process model 100 in accordance with one embodiment. In some embodiments of the heterogeneous process model 100 no specific configuration file 104 exists. Instead, the information that would otherwise be included in the configuration file 104 may be coded directly into to the model or provided to the modelling engine using another appropriate means. As described above the configuration file 104 includes the information required to apply the heterogeneous process model 100 to a particular biochemical environment. The configuration file 104 may be comprised of a number of sub-files including a molecule file 400, a process file 402, a designation file 404, a simulation parameter file 406, and an initial conditions file 408. Each of the aforementioned sub-files includes information utilized in the configuration of the heterogeneous process model 100, however, the information need not be divided into the specific sub-files described herein, depending on the embodiment.

The molecule file 400 includes molecules that have been selected to be simulated by the heterogeneous process model 100. In some embodiments, the molecule file 400 is a list of direct references to representations of molecules in a database. In embodiments utilizing a bipartite biochemical database 200, the molecule file 400 may be comprised of a list of direct references to molecule nodes 202 in the bipartite biochemical database 200. The molecule file 400 need not include a comprehensive list of every molecule included in the biochemical environment to be simulated. Instead, additional molecules that may be present in the biochemical environment can be determined by traversing the bipartite biochemical database 200 or by referencing the component molecule metadata field 218 of the molecule nodes 202 listed in the molecule file 400. This process of determining a full list of molecules for a simulation is further described with reference to FIG. 5.

The process file 402 includes processes that have been selected to be simulated by the heterogeneous process model 100. In some embodiments the process file 402 is a list of direct reference to representations of biochemical processes in a database. In embodiments utilizing a bipartite biochemical database 200, the process file 402 may be comprised of a list of direct references to process nodes 204 in the bipartite biochemical database 200. The process file 402 need not include a comprehensive list of every process included in the biochemical environment to be simulated. Instead, additional process that may occur in the biochemical environment can be determined by traversing the bipartite biochemical database 200 or by referencing the sub-processes metadata field 226 of the process nodes 204 listed in the process file 402. This process of determining the full list of processes for a simulation is described with reference to FIG. 5.

The designation file 404 includes information specifying which of the processes included in the process file 402 are to be simulated using a detailed model, and which are to be simulated using FBA. Additionally, the designation file 404 indicates the type of model to be used for each of the detailed models as well as the processes that will be considered internal exchange fluxes for the FBA analysis. In some embodiments, the designation file 404 also specifies how the internal exchange fluxes are integrated into the FBA. For instance, an internal exchange flux may be integrated with the model by setting the value of a flux variable in the flux vector of the FBA to a value determined by the detailed model. In this case, when the FBA portion of the heterogeneous model is solved using FBA's linear programming there would be one fewer variable to consider in the solution space. Alternatively, the internal exchange flux value can be determined by the detailed model and then used as a constraint during the linear programming step of the FBA. The interface between the detailed models is further described with reference to FIG. 6. Furthermore, the designation file 404 may specify whether the heterogeneous process model 100 is modelling a dynamic or steady state solution for a biochemical system. If the heterogeneous process model 100 is being used to model a steady state solution the heterogeneous process model 100 seeks a steady state solution to the detailed models and completes a single iteration of the FBA. If the heterogeneous process model 100 is being used to determine a dynamic solution, the detailed models progress for a predetermined time stamp before reporting the value of the exchange fluxes for use in an iteration of the FBA. This process is also further described with reference to FIG. 6.

The simulation parameter file 406 includes information specifying the parameters for the FBA and each of the detailed models designated in the designation file 404. The parameter information may include information specifying the objective function for the FBA as well as any constants that may be used for the detailed models. In some embodiments, the parameter file also includes constraints on the solution space of the FBA in accordance with the limits of known biochemical fluxes for particular process. Additionally, the simulation parameter file 406 may include minimum or maximum thresholds for the molecules included in the heterogeneous process model 100. In some embodiments, where the time step of the heterogeneous process model 100 can be modified, the simulation parameter also includes the duration of the time step of the simulation.

Initial conditions file 408 includes information specifying the initial environmental conditions of the biochemical environment being simulated by the heterogeneous process model 100. Depending on the specific embodiment, environmental conditions may include but are not limited to: the initial concentrations of each of the molecules identified in the molecule file 400, the temperature of the environment (or temperature profile if the environment is not assumed to be of uniform temperature), the pressure of the environment, and the physical geometry of the environment. Although the FBA component of the heterogeneous process model 100 does not consider environmental conditions in the solution, detailed models may require environmental conditions in order to determine a solution. Furthermore, the solution state of the heterogeneous process model 100 includes the concentration of all molecules in the heterogeneous process model 100 in addition to each of the flux values describing the transitions between those molecules. Thus, initial concentrations of each of the molecules involved in the heterogeneous process model 100 may be included in the initial conditions file 408. Additionally, the initial conditions file 408 may specify the value of the external exchange fluxes for the FBA component of the heterogeneous process model 100.

VI. Compiling the Heterogeneous Process Model

Figure 5:
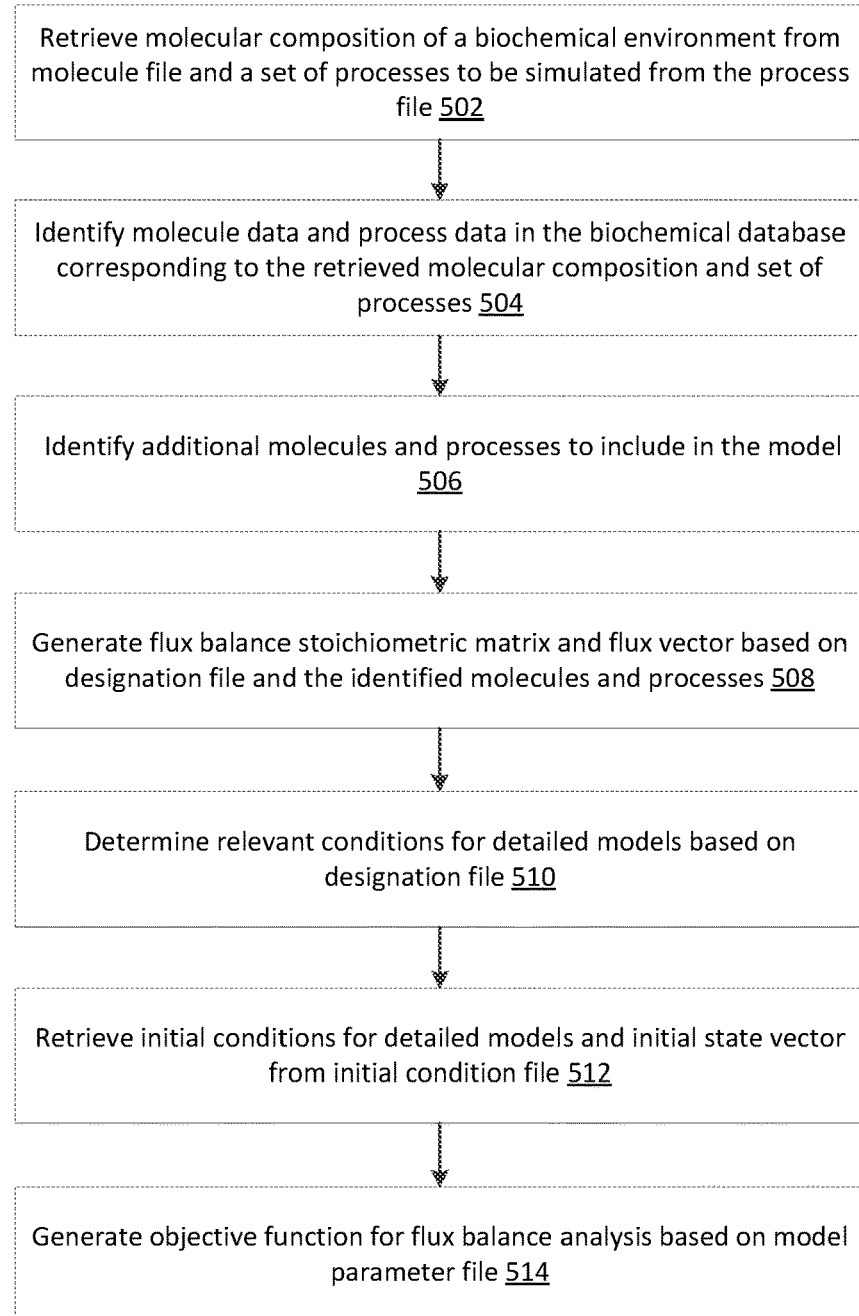
FIG. 5 is a block diagram illustrating a compilation method for a heterogeneous process model in accordance with one embodiment.

FIG. 5 is a block diagram illustrating a compilation method 500 for a heterogeneous process model 100 in accordance with one embodiment. The compilation method 500 illustrated in FIG. 5 is performed by the model compiler 106 or other equivalent program and leverages the data stored in the biochemical database 102 and the configuration file 104. The model compiler 106 begins by retrieving 502 the molecular composition of a biochemical environment to be simulated from the molecule file 400. Depending on the embodiment, the model compiler 106 may also retrieve 502 a set of processes to be simulated in the heterogeneous process model 100.

After retrieving the information from the molecule file 400 and the process file 402, the model compiler 106 identifies 504 molecule data and process data in the biochemical database 102 corresponding to the retrieved molecular composition and set of processes. In embodiments utilizing a bipartite biochemical database 200, the model compiler 106 identifies the molecule nodes 202 and process nodes 204 corresponding to the retrieved molecule and process information. The model compiler 106 then identifies 506 additional molecules and processes for inclusion in the model by traversing the biochemical database 102 beginning at the previously identified molecules and processes in the database.

In embodiments utilizing a bipartite biochemical database 200, the model compiler 106 traverses the bipartite biochemical database 200 to identify process nodes 204 and molecule nodes 202 associated with the identified molecule nodes 202 and process nodes 204 corresponding the received molecule and process information. In embodiment where the bipartite biochemical database 200 is a directed graph, the traversal of the graph would follow the directionality of the roles 228. Alternatively, process nodes 204 are not identified as associated with the identified set of molecule nodes 202 unless all of the product/reactant roles of the process are filed by one of the identified molecule nodes 202. The additional molecule nodes identified in the graph traversal (as opposed to being received in the molecular composition data) may be transitional molecules between sub-processes not included in the received molecular composition data. These additional molecular may inform researchers of additional molecules that may be present in a biochemical environment that were not previously detected. One of skill in the art will recognize that many graph traversal algorithms may be used, including both breadth-first-search or depth-first-search, depending on the embodiment.

In some embodiments, after traversing the bipartite biochemical database 200 to identify process nodes 204 and addition molecule nodes 202, "dead-end" molecule nodes may be pruned from the identified set of nodes, depending on the embodiment. "Dead-end" nodes are molecule nodes 202 that have no identified processes for which they are a reactant/substrate or have no identified processes for which they are a product. Physically, these dead-end molecules could not accumulate or be consumed without an additional processes that are not in the database or are not possible for a given biochemical environment. For these reasons, these molecules are pruned from the identified molecule nodes 202, and depending on the embodiment may be identified for further research. In some embodiments, the pruning process may be recursive in that once the first set of dead-end molecules nodes have been removed from the identified set, the recursive processes determines if any process nodes are left without all of the associated roles occupied. If any processes are identified then they are pruned from the identified set as well, which would cause the recursive process to continue to a next step of pruning dead-end molecule nodes.

After the traversal of the biochemical database 102, and the identification of molecules and processes to be included in the heterogeneous process model 100, the model compiler 106 generates 508 a stoichiometric matrix and flux vector based on the designation file 404 and the identified molecules and processes to be included in the heterogeneous process model 100. As previously described with respect to FIG. 4, the designation file 404 identifies which of the molecules and processes are to be simulated using the FBA component of the heterogeneous process model 100. The molecules that are identified by the designation file 404 as being simulated by the FBA are each represented as a row in the stoichiometric matrix. The number of columns in the stoichiometry corresponds to the number of processes that have been identified in the designation file 404 as being simulated by the FBA component of the heterogeneous process model 100 in addition to all processes that include exchange fluxes (either external or internal). Thus, each position (row-column combination) in the stoichiometric matrix is populated with the stoichiometric coefficient corresponding to the molecule represented by the row in the process represented by the column. In this manner, the model compiler 106 populates the stoichiometric matrix. In embodiments utilizing a bipartite biochemical database 200, the model compiler 106 retrieves the roles 228 associated with the molecule and process corresponding to the position in the stoichiometric matrix.

After generating the stoichiometric matrix and the flux vector for the FBA component of the heterogeneous process model 100, the model compiler 106 determines 510 the relevant conditions for the detailed models of the heterogeneous process model 100, based on the designation file 404. For example, depending on the type of detailed model being used temperature and pressure may be needed for the model in addition to the concentrations of each molecule being simulated by the detailed model. Upon determining the relevant conditions, the model compiler 106 retrieves 512, those conditions from the initial condition file 408. The model compiler 106 then generates 514 an objective function for the FBA component of the model based on data from the parameter file 406. After the compilation process has been completed, the heterogeneous process model 100 can initiate a simulation of a biochemical environment.

VII. Simulation Using a Heterogeneous Process Model

Figure 6:
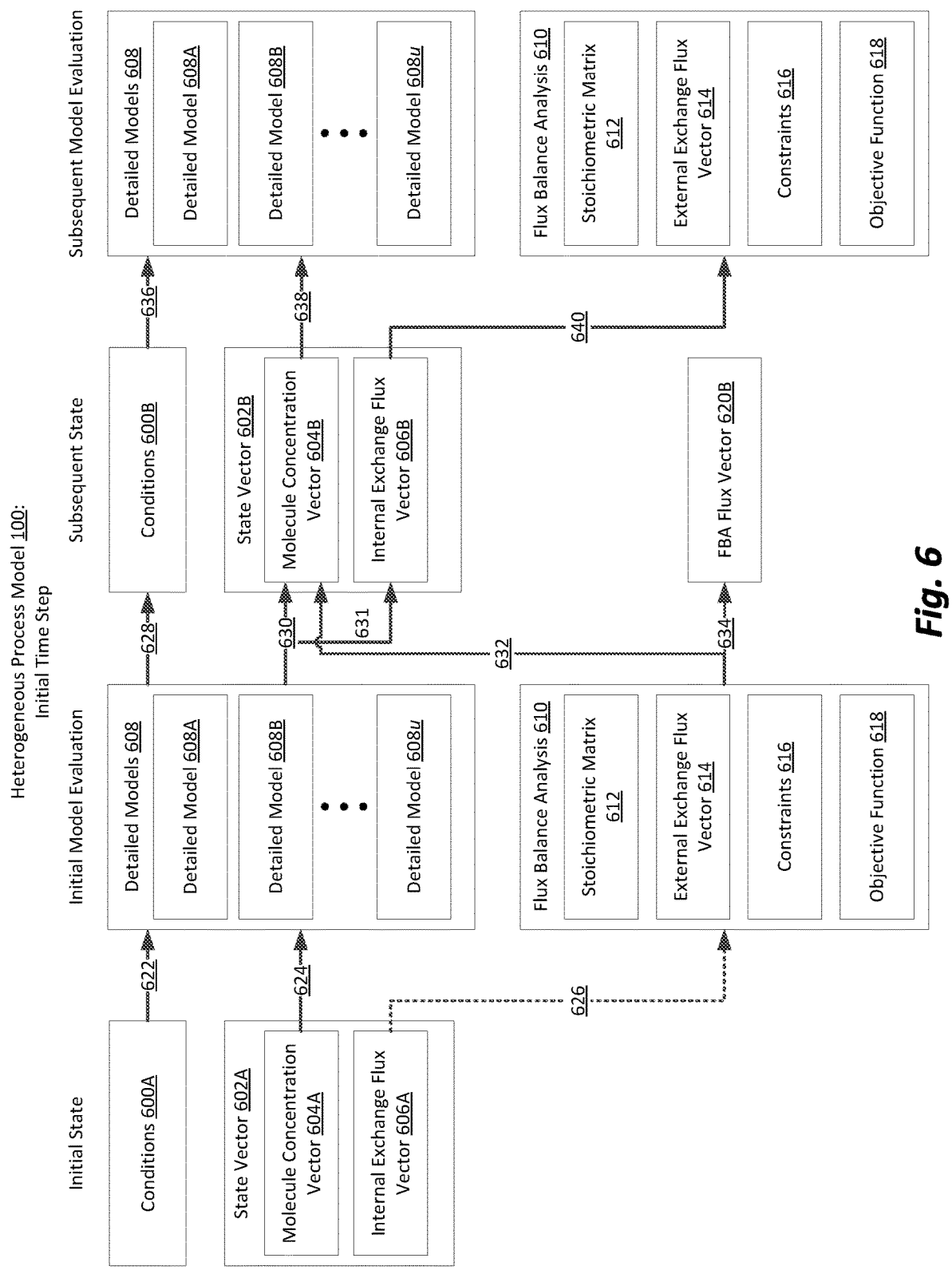
FIG. 6 is a flow diagram illustrating one time step of the heterogeneous process model in accordance with one embodiment.

FIG. 6 is a flow diagram illustrating one time step of the heterogeneous process model 100 in accordance with one embodiment. FIG. 6 illustrates the different data sets and sub-models that may comprise the heterogeneous process model 100 and the interactions between those entities that may result in a time dependent simulation of a large scale biochemical environment. The illustrated process is organized into four separate steps: an initial state, an initial model evaluation, a subsequent state, and a subsequent model evaluation.

Evaluating a model may include the performance of a series of calculations resulting in an output of a model or analysis. For example, evaluating a flux balance analysis may include performing a flux balance analysis using inputs such as a flux vector, stoichiometric matrix, and objective function through linear programming or other means known in the art. The evaluation of the flux balance analysis may then result in an output of a calculated solution flux vector. Likewise, an evaluation of a detailed model may include calculating a set of output conditions (e.g. molecule concentrations) based on a set of input conditions in a manner that depends on the particular detailed model. For detailed models that provide time dependent solutions, evaluating the detailed model may also include calculating the solution state at any particular time after an initial time.

The initial state of the heterogeneous process model 100 is defined by a set of initial conditions for the model 600A and a state vector 602A. The state vector 602A is further comprised of molecule concentration vector 604A, which contains the initial concentrations of each molecule involved in the heterogeneous process model 100. In some embodiments, the initial state vector 602A may also include an initial internal exchange flux vector 606A, providing initial values for the internal exchange fluxes that would otherwise be defined by the detailed models. In alternative embodiments, the FBA component of the heterogeneous process model 100 is evaluated (in a second time step) after the detailed models have been initially evaluated (in a first time step).

The initial state of the heterogeneous process model 100 is evaluated using at least two model components including one or more detailed models 608A, 608B, . . . , 608u, and a flux balance analysis 610. The flux balance analysis 608 is comprised of a stoichiometric matrix 612, an external exchange flux vector 614, constraints 616, and an objective function 618, all of which were generated using the model compiler 106 in preparation for the simulation. Thus, the flux balance analysis 610 can be completed as known in the art assuming an initial internal exchange flux vector 606A is provided.

For the initial time step of the heterogeneous process model 100, the detailed models 608 retrieve 622 the initial conditions 600A and retrieve 624 the initial molecule concentrations 604A and calculate a solution state for the respective processes represented by each of the detailed models 608 one time step from the initial state, where the time step is a predetermined interval of time.

Meanwhile, the flux balance analysis 610 may be evaluated after retrieving 626 the initial exchange flux values 606A. In embodiments where no initial exchange flux values 606A are provided, the flux balance analysis may alternatively allow the internal exchange fluxes in to be variable like the other fluxes in the flux vector. In cases where, the internal exchange fluxes are allowed to be variable for a first iteration internal exchange flux constraints are set in the constraints of the flux balance analysis 610. Otherwise the flux balance analysis 610 is evaluated as known in the art for the first iteration of the heterogeneous process model 100.

The results of the initial model evaluation are used to determine the subsequent state for the model. The subsequent state is defined by a new set of conditions 600B and a new state vector 602B, including a new set of molecule concentrations 604B and a new internal exchange flux vector 606B. In embodiments where the detailed models 608 affect the conditions of the physical environment (for example by changing the temperature via flux through an endothermic or exothermic reaction) the conditions 600B are updated 628 to reflect the solutions to the detailed models 608. In some embodiments, the energy requirements, or other characteristics that may affect the conditions 600, are known for the processes being simulated by the flux balance analysis 610 and so the result of the flux balance analysis 610 may also be used to modify conditions 600B from the initial conditions in 600A. Additionally, the solutions to the one or more detailed models 608 are used to determine 630 the molecule concentrations 604B for the molecules included in the detailed models 608. Furthermore, the solution of the detailed models determines 631 an internal exchange flux vector 606B, which is used to solve the flux balance analysis 610 in the subsequent iteration of the model for the subsequent time step.

Meanwhile, the results of the flux balance analysis 610 are also applied to the subsequent solution state for the heterogeneous process model 100. The solution of the flux balance analysis 610, which is in the form of a flux vector, is used to modify the initial molecule concentrations 604A by multiplying the determined net flux for each molecule (based on the flux vector) by the predetermined time stamp to determine a net change in the concentration of each molecule simulated by flux balance analysis 610. This information is used to determine 632 the new molecule concentrations 604B for state vector 602B along with the results of the determined models 608. Thus, the results of both model types determine the subsequent state for the model. The FBA flux vector 620B is also included 634 in the subsequent solution state of the heterogeneous process model 100.

After the subsequent solution state has been determined, the model progresses to a subsequent model evaluation for a second time step. The subsequent set of conditions 600B (optionally codetermined by both the detailed models and the flux balance analysis 610) are used as input 636 into the second iteration of each of the detailed models 608 along with 638 the subsequent set of molecule concentrations 604B, such that the detailed models 608 may be evaluated, dynamically, for a second time step.

Additionally, the flux balance analysis 610 is evaluated for a second time. However, instead of having variable or preset internal exchange fluxes, as in the first evaluation of the model, for each subsequent evaluation, the flux balance analysis 610 integrates 640 the internal exchange flux vector 606B calculated by the detailed models 608 in the previous evaluation step of the model. In some embodiments, this is accomplished by setting the value of the internal exchange fluxes in the flux vector of the flux balance analysis 610 directly. In other embodiments, the internal exchange flux in the flux vector are allowed to vary within a small interval of fluxes corresponding to a margin of error of a corresponding detailed model. Alternatively, the value of the internal exchange fluxes may be a function of the value determined in the first iteration of the flux balance analysis 610 and the values of the internal exchange flux vector 606B, determined by the detailed models.

Once the subsequent state data is integrated in the subsequent iteration of the heterogeneous process model 100, the iteration may continue following the steps described in steps 628, 630, 631, 632, 634, 636, 638, and 640 for each subsequent time step. In this way, the two model types can be continuously reevaluated to determine a time-dependent solution for a complex biochemical environment, while minimizing computational resources only where they are needed (in the detailed models). The evaluation of the model may continue for a predetermined number of time steps (e.g. to achieve a particular model duration) or may continue until a termination state is reached, for example, the achievement of a steady state solution or any other condition determined by a user.

VIII. Additional Considerations

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof. In one embodiment, a software module is implemented with a computer program product comprising a persistent computer-readable medium containing computer program code, which can be executed by a computer processor for performing any or all of the steps, operations, or processes described.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, an example of which is set forth in the following claims.

What is claimed is:

1. A computer-implemented method for simulating a biochemical environment comprising:
   accessing a bipartite biochemical database comprising a plurality of molecule entries and a plurality of process entries, the bipartite biochemical database including a role and an initial concentration for each molecule entry in at least one of the process entries;
   accessing a configuration file containing instructions for configuring a heterogeneous process model, wherein the heterogeneous process model includes a flux balance analysis model and one or more time-dependent detailed models, and wherein the configuration file designates one or more process entries of the plurality of process entries corresponding with the one or more time-dependent detailed models;

assigning, based on the roles included in the bipartite biochemical database and the one or more process entries of the plurality of process entries designated in the configuration file, a first set of the plurality of molecule entries and a first set of the plurality of process entries to the flux balance analysis model, wherein the assigning includes defining an initial internal exchange vector for the flux balance analysis model;

assigning, based on the roles included in the bipartite biochemical database and the one or more process entries of the plurality of process entries designated in the configuration file, a second set of the plurality of molecule entries and a second set of the plurality of process entries including the one or more process entries to the one or more time-dependent detailed models, wherein the assigning includes defining an initial concentration vector using the initial concentration from the bipartite biochemical database and an initial condition vector for the one or more time-dependent detailed models;

determining an initial state of the heterogeneous process model by:
 applying the flux balance analysis model to the initial internal exchange vector to produce an initial solution flux vector, and
 applying the one or more time-dependent detailed models to the initial concentration vector and initial condition vector to produce a concentration vector, a condition vector, and an internal exchange flux vector; and determining subsequent states of the heterogeneous process model for a plurality of time steps by:
 applying the flux balance analysis model to an internal exchange flux vector produced in a prior time step to produce a solution flux vector, and
 applying the one or more time-dependent detailed models to a concentration vector and a condition vector produced in a prior time step to update the concentration vector, the condition vector, and an internal exchange flux vector.

2. The method of claim 1, further comprising:
compiling the heterogeneous process model including:
a stoichiometric matrix in the flux balance analysis model including a stoichiometric coefficient corresponding to the role of each molecule entry in the first set of the plurality of molecule entries in at least one of the process entries of the first set of the plurality of process entries.

3. The method of claim 1, wherein each value in the initial internal exchange vector represents a flux of a molecule in one of the second set of the plurality of process entries simulated by one or more time-dependent detailed models, and wherein each molecule entry in the second set of the plurality of molecules entries is associated with a different molecule than each molecule entry in the first set of the plurality of molecule entries.

4. The method of claim 1, wherein the configuration file further defines:
 each of the first set of the plurality of molecule entries as having at least one role in the first set of the plurality of process entries,
 each of the second set of the plurality of molecule entries as having at least one role in the second set of the plurality of process entries,
 one or more exchange molecule entries of the second set of the plurality of molecule entries as having at least one exchange role in the first set of the plurality of process entries, and
 internal exchange fluxes as corresponding to the at least one exchange role in the one or more exchange molecule entries.

5. The method of claim 1, wherein the role is characterized as one of:
 a substrate,
 a reactant,
 a catalyst,
 a cofactor, or
 a product.

6. The method of claim 1, further comprising:
compiling the heterogeneous process model including a set of initial conditions of the biochemical environment included in the configuration file, wherein the set of initial conditions includes a temperature, a pressure, or a geometry of the biochemical environment, and wherein the initial condition vector includes the set of initial conditions.

7. The method of claim 1, wherein the one or more time-dependent detailed models includes one or more of:
 an ordinary differential equation model,
 a stochastic differential equation model, or
 a Monte Carlo model.

8. The method of claim 1, wherein applying the flux balance analysis model further comprises:
evaluating the solution flux vector for the first set of the plurality of molecule entries based on an objective function.

9. The method of claim 8, wherein evaluating the solution flux vector for the first set of the plurality of molecule entries further comprises:
maximizing the objective function in the flux balance analysis model.

10. The method of claim 8, wherein applying the flux balance analysis model to the initial internal exchange vector to produce the initial solution flux vector for the first set of the plurality of molecule entries further comprises:
minimizing the objective function in the flux balance analysis model.

11. The method of claim 1, wherein updating the concentration vector further comprises, calculating a product of the solution flux vector and a predetermined interval of time, and adding a resulting product to the concentration vector produced in a prior time step.

12. The method of claim 1, wherein the configuration file comprises one or more sub-files, each sub-file containing instructions for configuring a heterogeneous process model.

13. The method of claim 1, wherein a second set of initial conditions includes an initial concentration for each molecule in the second set of the plurality of molecule entries and one or more of a temperature of an environment, a pressure of the environment, a physical geometry of the environment.

14. The method of claim 1, wherein the flux balance analysis model includes an external exchange flux vector, a set of constraints, and an objective function.

15. The method of claim 1, further comprising:
compiling the configuration file for configuring the heterogeneous process model using the bipartite biochemical database; and
simulating the biochemical environment using the compiled configuration file, wherein the simulating comprises:
determining an initial state of the heterogeneous process model by:
applying the flux balance analysis model to the initial internal exchange vector to produce an initial solution flux vector, and
applying the one or more time-dependent detailed models to the initial concentration vector and initial condition vector to produce a concentration vector, a condition vector, and an internal exchange flux vector; and
determining subsequent states of the heterogeneous process model for a plurality of time steps by:
applying the flux balance analysis model to an internal exchange flux vector produced in a prior time step to produce a solution flux vector, and
applying the one or more time-dependent detailed models to a concentration vector and a condition vector produced in a prior time step to update the concentration vector, the condition vector, and an internal exchange flux vector.

16. A system for simulating a biochemical environment comprising:
a processor; and
a non-transitory computer-readable storage medium storing instructions causing the processor to:
access a bipartite biochemical database comprising a plurality of molecule entries and a plurality of process entries, the bipartite biochemical database including a role and an initial concentration for each molecule entry in at least one of the process entries;
access a configuration file containing instructions for configuring a heterogeneous process model, wherein the heterogeneous process model includes a flux balance analysis model and one or more time-dependent detailed models, and wherein the configuration file designates one or more process entries of the plurality of process entries corresponding with the one or more time-dependent detailed models;
assign, based on the roles included in the bipartite biochemical database and the one or more process entries of the plurality of process entries designated in the configuration file, a first set of the plurality of molecule entries and a first set of the plurality of process entries to the flux balance analysis model, wherein the assigning includes defining an initial internal exchange vector for the flux balance analysis model;
assign, based on the roles included in the bipartite biochemical database and the one or more process entries of the plurality of process entries designated in the configuration file, a second set of the plurality of molecule entries and a second set of the plurality of process entries including the one or more process entries to the one or more time-dependent detailed models, wherein the assigning includes defining an initial concentration vector using the initial concentration from the bipartite biochemical database and an initial condition vector for the one or more time-dependent detailed models;
determine an initial state of the heterogeneous process model by:
apply the flux balance analysis model to the initial internal exchange vector to produce an initial solution flux vector, and
apply the one or more time-dependent detailed models to the initial concentration vector and initial condition vector to produce a concentration vector, a condition vector, and an internal exchange flux vector; and
determine subsequent states of the heterogeneous process model for a plurality of time steps by:
applying the flux balance analysis model to an internal exchange flux vector produced in a prior time step to produce a solution flux vector, and
applying the one or more time-dependent detailed models to a concentration vector and a condition vector produced in a prior time step to update the concentration vector, the condition vector, and an internal exchange flux vector.

17. The system of claim 16, further comprising instructions to cause the processor to:
compile the heterogeneous process model including:
a stoichiometric matrix in the flux balance analysis model including a stoichiometric coefficient corresponding to the role of each molecule entry in the first set of the plurality of molecule entries in at least one of the process entries in the first set of the plurality of process entries.

18. The system of claim 16, wherein each value in the initial internal exchange vector represents a flux of a molecule in one of the second set of the plurality of process entries simulated by one or more time-dependent detailed models, and
wherein each molecule entry in the second set of the plurality of molecules entries is associated with a different molecule than each molecule entry in the first set of the plurality of molecule entries.

19. The system of claim 16, wherein the configuration file further defines:
each of the first set of the plurality of molecule entries as having at least one role in the first set of the plurality of process entries,
each of the second set of the plurality of molecule entries as having at least one role in the second set of the plurality of process entries,
one or more exchange molecule entries of the second set of the plurality of molecule entries as having at least one exchange role in the first set of the plurality of process entries, and
internal exchange fluxes as corresponding to the at least one exchange role in the one or more exchange molecule entries.

20. The system of claim 16 further comprising instruction to causes the processor to:
compile the heterogeneous process model including a set of initial conditions of the biochemical environment included in the configuration file, wherein the set of initial conditions includes a temperature, a pressure, or a geometry of the biochemical environment, and wherein the initial condition vector includes the set of initial conditions.

21. The system of claim 16, wherein the one or more time-dependent detailed models includes one or more of:
an ordinary differential equation model,
a stochastic differential equation model, or
a Monte Carlo model.

22. The system of claim 16, wherein updating the concentration vector further comprises, calculating a product of the solution flux vector and a predetermined interval of time, and adding a resulting product to the concentration vector produced in a prior time step.

23. The system of claim 16, wherein applying the flux balance analysis model further comprises:
evaluating the solution flux vector for the first set of the plurality of molecule entries based on an objective function.

24. The system of claim 16, further comprising:
compiling the configuration file for configuring the heterogeneous process model using the bipartite biochemical database; and
simulating the biochemical environment using the compiled configuration file, wherein the simulating comprises:
determining an initial state of the heterogeneous process model by:
applying the flux balance analysis model to the initial internal exchange vector to produce an initial solution flux vector, and
applying the one or more time-dependent detailed models to the initial concentration vector and initial condition vector to produce a concentration vector, a condition vector, and an internal exchange flux vector; and
determining subsequent states of the heterogeneous process model for a plurality of time steps by:
applying the flux balance analysis model to an internal exchange flux vector produced in a prior time step to produce a solution flux vector, and
applying the one or more time-dependent detailed models to a concentration vector and a condition vector produced in a prior time step to update the concentration vector, the condition vector, and an internal exchange flux vector.

25. A non-transitory computer readable storage medium storing instructions for simulating a biochemical environment comprising:
accessing a bipartite biochemical database comprising a plurality of molecule entries and a plurality of process entries, the bipartite biochemical database including a role and an initial concentration for each molecule entry in at least one of the process entries;
accessing a configuration file containing instructions for configuring a heterogeneous process model, wherein the heterogeneous process model includes a flux balance analysis model and one or more time-dependent detailed models, and wherein the configuration file designates one or more process entries of the plurality of process entries corresponding with the one or more time-dependent detailed models;
assigning, based on the roles included in the bipartite biochemical database and the one or more process entries of the plurality of process entries designated in the configuration file, a first set of the plurality of molecule entries to the flux balance analysis model, wherein the assigning includes defining an initial internal exchange vector for the flux balance analysis model;
assigning, based on the roles included in the bipartite biochemical database and the one or more process entries of the plurality of process entries designated in the configuration file, a second set of the plurality of molecule entries and a second set of the plurality of process entries including the one or more process entries to the one or more time-dependent detailed models, wherein the assigning includes defining an initial concentration vector using the initial concentration from the bipartite biochemical database and an initial condition vector for the one or more time-dependent detailed models;
determining an initial state of the heterogeneous process model by:
applying the flux balance analysis model to the initial internal exchange vector to produce an initial solution flux vector, and
applying the one or more time-dependent detailed models to the initial concentration vector and initial condition vector to produce a concentration vector, a condition vector, and an internal exchange flux vector; and
determining subsequent states of the heterogeneous process model for a plurality of time steps by:
applying the flux balance analysis model to an internal exchange flux vector produced in a prior time step to produce a solution flux vector, and
applying the one or more time-dependent detailed models to a concentration vector and a condition vector produced in a prior time step to update the concentration vector, the condition vector, and an internal exchange flux vector.

26. The non-transitory computer readable storage medium of claim 25, further comprising:
compiling a heterogeneous process model including:
a stoichiometric matrix in the flux balance analysis model including a stoichiometric coefficient corresponding to the role of each molecule entry in the first set of the plurality of molecule entries in at least one of the process entries in the first set of the plurality of process entries.

27. The non-transitory computer readable storage medium of claim 25, wherein each value in the initial internal exchange vector represents a flux of a molecule in one of the second set of the plurality of process entries simulated by one or more time-dependent detailed models, and
wherein each molecule entry in the second set of the plurality of molecules entries is associated with a different molecule than each molecule entry in the first set of the plurality of molecule entries.

28. The non-transitory computer readable storage medium of claim 25, wherein each of the first set of the plurality of molecule entries have at least one role in the first set of the plurality of process entries,
wherein each of the second set of the plurality of molecule entries have at least one role in the second set of the plurality of process entries,
wherein one or more exchange molecule entries of the second set of the plurality of molecule entries have at least one exchange role in the first set of the plurality of process entries, and
wherein internal exchange fluxes correspond to the at least one exchange role in the one or more exchange molecule entries.

29. The non-transitory computer readable storage medium of claim 25, further comprising:
compiling a heterogeneous process model including a set of initial conditions of the biochemical environment included in the configuration file, wherein the set of initial conditions includes a temperature, a pressure, or a geometry of the biochemical environment, and wherein the initial condition vector includes the set of initial conditions.

30. The non-transitory computer readable storage medium of claim 25, wherein the one or more time-dependent detailed models includes one or more of:

an ordinary differential equation model,
a stochastic differential equation model, or
a Monte Carlo model.

31. The non-transitory computer readable storage medium of claim 25, wherein applying the flux balance analysis model further comprises:
evaluating the solution flux vector for the first set of the plurality of molecule entries based on an objective function.

32. The non-transitory computer readable storage medium of claim 25, wherein the configuration file comprises one or more sub-files, each sub-file containing instructions for configuring a heterogeneous process model.

33. The non-transitory computer readable storage medium of claim 25, further comprising:
compiling the configuration file for configuring the heterogeneous process model using the bipartite biochemical database; and
simulating the biochemical environment using the compiled configuration file, wherein the simulating comprises:
determining an initial state of the heterogeneous process model by:
applying the flux balance analysis model to the initial internal exchange vector to produce an initial solution flux vector, and
applying the one or more time-dependent detailed models to the initial concentration vector and initial condition vector to produce a concentration vector, a condition vector, and an internal exchange flux vector; and
determining subsequent states of the heterogeneous process model for a plurality of time steps by:
applying the flux balance analysis model to an internal exchange flux vector produced in a prior time step to produce a solution flux vector, and
applying the one or more time-dependent detailed models to a concentration vector and a condition vector produced in a prior time step to update the concentration vector, the condition vector, and an internal exchange flux vector.

* * * * *